United States Patent [19]
Burgi et al.

[11] Patent Number: 5,666,435
[45] Date of Patent: Sep. 9, 1997

[54] SYSTEM FOR ANALYSIS OF X-RAY FILMS OF NUCLEOTIDE SEQUENCES

[75] Inventors: Dean S. Burgi, Menlo Park; Daniel M. Bartell, Foster City; Donald D. Sleeter, San Leandro; Lucina P. Mastro, San Francisco, all of Calif.

[73] Assignee: Genomyx Corporation, Foster City, Calif.

[21] Appl. No.: 354,412

[22] Filed: Dec. 9, 1994

[51] Int. Cl.⁶ .................................................. G06K 9/00
[52] U.S. Cl. ............................................ 382/129; 382/181
[58] Field of Search ................................ 382/128, 129, 382/168, 173, 181, 190, 191, 192, 203, 209, 254, 312; 364/413.16, 413.17, 413.18, 413.01, 413.02, 413.03, 413.04, 413.05; 250/583, 909

[56] References Cited

U.S. PATENT DOCUMENTS

| | | | |
|---|---|---|---|
| 4,841,443 | 6/1989 | Kakumoto et al. | 382/129 |
| 4,852,050 | 7/1989 | Shiraishi et al. | 382/129 |
| 4,862,358 | 8/1989 | Kimura et al. | 382/129 |
| 4,862,360 | 8/1989 | Kimura et al. | 382/129 |
| 4,884,200 | 11/1989 | Kimura et al. | 382/129 |
| 4,980,827 | 12/1990 | Hara | 382/129 |
| 5,273,632 | 12/1993 | Stockham et al. | 204/180.1 |
| 5,400,249 | 3/1995 | Soll et al. | 364/413.01 |
| 5,419,825 | 5/1995 | Fujii | 364/413.01 |

OTHER PUBLICATIONS

Automated DNA sequencing: an image processing approach; Yecheng Wu & David Mislan; Applied and Theoretical Electrohophoresis (1993) 3, Macmillan Press, pp. 223–2238. (No place of publication).

An adaptive, object oriented strategy for base calling in DNA sequence analysis; Michael C. Giddings, Robert L. Brumley Jr., Michael Haker and Lloyd M. Smith; Nucleic Acids Research, 1993, vol. 21, No. 19, 1993 Oxford University Press, pp. 4530–4540.

Quantitative Analysis of Electrophoretograms: A Mathematical Approach to Super–Resolution; Analytical Biochemistry 111, pp. 257–268 (1981); D.A. Agard, R.A. Steinberg, R.M. Stroud; Department of Biochemistry & Biophysics, Universit of California, School of Medicine.

*Primary Examiner*—Leo Boudreau
*Assistant Examiner*—Bijan Tadayon
*Attorney, Agent, or Firm*—McDonnell, Boehnen, Hulbert & Berghoff

[57] ABSTRACT

A system for identification of DNA bases in a nucleotide sequence includes a microprocessor and a set of executable instructions and is configured to accept a set of input data corresponding to a DNA sequence image from an autoradiograph. In part by interpolating a distribution of density peaks derived from the set of input data, the system is configured to generate a set of output data substantially identifying or presenting the bases in the DNA sequence in a linear fashion, corresponding to the linear order of nucleotides comprising the DNA sequence. The system thereby enables identification of substantially more bases than could be read by the human eye. Enhanced electrophoresis equipment and consumables may also be applied to generate a more predictable and linear set of input data and, in turn, to generate a set of output data identifying an even greater number of DNA bases in the sequence under analysis.

21 Claims, 4 Drawing Sheets

Microfiche Appendix Included
(8 Microfiche, 719 Pages)

SYSTEM FOR ANALYSIS OF X-RAY FILMS OF NUCLEOTIDE SEQUENCES

MICROFICHE APPENDIX

This application contains a microfiche appendix, which consists of 8 sheets of microfiche and a total of 719 frames.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to the analysis of x-ray films of DNA nucleotide sequences. More particularly, the present invention relates to an improved system for processing an autoradiograph image of a nucleotide sequence in order to more accurately and extensively read and identify the bases comprising the nucleotide sequence of a given nucleic acid.

BACKGROUND OF THE INVENTION

Autoradiographs, or x-ray films, of nucleotide sequences are typically generated by a fundamental biochemical technique incorporating a process known as gel electrophoresis. Gel electrophoresis is a procedure that enables single-stranded DNA fragment molecules of a nucleic acid to be distinguished on the basis of size and/or charge. Electrophoresis is usually performed in a gelled (e.g., agarose) or polymerized (e.g., polyacrylamide) media (generically termed a "gel") that contains an electrically conducting buffer. Electrophoresis entails the application of a voltage via chemically inert metal electrodes across the cross-sectional area of the gel. The nucleic acid of interest is placed into pre-formed sample wells in the gel, usually at one end of the gel, and the polarity of the applied voltage is arranged so that the nucleic acid sample migrates through the gel towards one of the electrodes (usually positioned at the opposite end of the gel from the samples). Where appropriate, the inverse linear relationship between migration distance and molecular size is maintained by the addition of chemical denaturants (such as urea, formamide, or sodium dodecyl sulfate) to the gel and electrophoresis buffer.

Prior to conducting gel electrophoresis, a collection of single-stranded DNA fragments is generated either by chemical degradation of the nucleic acid (using the Gilbert method, see e.g., Maxam and Gilbert (1980), Methods Enzymeol., 65, 499–500) or most frequently by replacement DNA synthesis using a polymerase (using the Sanger method, see e.g., Sanger, F., Niklen, S., and Coulson, A. R. (1977) Proc. Natl. Acad. Sci. U.S.A. 74, 5463–5467). This collection of single-stranded DNA fragments includes a fragment corresponding to each position in the sequence to be determined. Typically, this correspondence is directly related to the distance from a fixed site of initiation of polymerization at a primer that is annealed to the nucleic acid to be sequenced. Thus, determination of the desired sequence depends on the separation of each of the fragments, which differ in length by only a single nucleotide.

As further described in the '583 application, the identity of each of the four possible nucleotides at each position (adenine ("A"), guanine ("G"), cytosine ("C") or thymidine ("T")) is traditionally distinguished by performing a sequencing reaction specific for each ending nucleotide in a separate chemical reaction mixture. Typically, each of the four sequencing experiments is performed in a separate test tube. In each test tube, a collection of fragments is generated, each fragment ending at a position corresponding to the terminating nucleotide used in the given reaction. To determine the nucleotide sequence of the nucleic acid sample, gel electrophoresis is next performed on each of the four reaction mixtures, samples of the four reactions being electrophoresed individually in adjacent lanes of a single sequencing gel.

As is well known in the art, in order to perform electrophoresis, each sample to be electrophoresed is first loaded in a well at approximately one end of the sequencing gel. During electrophoresis, the gel is then in contact with electric current-carrying buffer solutions and is placed between two electrodes. Application of direct current voltage across the gel is achieved by placing the positive electrode at the end distal to the loading wells (also known as the "bottom end") and the negative end at the end proximal to the loading wells (also known as the "top end.") Electrophoresis is then achieved when the DNA molecules, or fragments, are separated in a direction going from the negative electrode to the positive electrode, wherein the smallest molecules travel the farthest toward the positive end. As a result, in theory, the presence of a band at a position in a nucleotide-specific lane of the gel indicates the identity of that nucleotide at that position in the sequence.

Conventionally, each of the fragments is radiolabeled, and, after electrophoresis, the four lanes and bands in the sequencing gel are visualized by autoradiography on x-ray films. As a result, the images on the resulting autoradiographs should theoretically be precise depictions of the band positions in the gel. Unfortunately, however, the ability to identify band positions on an autoradiograph of a DNA sequence has suffered from certain limitations.

One principle factor affecting the ability to determine the presence of a band at a given position in a nucleotide-specific lane (or, more specifically, in the combined nucleic acid sequence) is the band resolution. As indicated in the '583 application, band resolution depends on the thickness of each band as well as the relationship between the average thickness of each band and the width of the space separating each band. A sequencing ladder comprised of thick bands will contain fewer resolvable bands on average than a gel having thinner, more tightly-resolved bands, as a result of the finite length of the resolvable portion of the gel. Additionally, since each of the bands in a sequencing gel can in principle differ in size by as few as one nucleotide, stretches of DNA containing doublets, triplets or more multiple repeats of a particular nucleotide (e.g., 5'-TTTTTTTTT-3') have been difficult to resolve in a gel. In turn, therefore, it has been difficult to read such nucleotide sequences on the resulting autoradiograph x-ray film as well.

Another related factor affecting the ability to identify bases in a DNA sequence is the broadening of base bands. Higher up in the gel, where there are many close bands, the bands are sufficiently broad that they overlap each other. To the unaided human eye, these overlapping bands are seen as one broad band.

Yet another factor affecting the ability to read DNA sequences on autoradiographs is the nonlinearity of conventional sequencing gels and electrophoresis processes. In view of the above noted proportionality between DNA molecule size and distance traveled from the top end of the sequencing gel to the bottom end of the sequencing gel, theory would dictate that a linear distribution should occur along the entire length of the gel and, in turn, along the entire length of the autoradiograph. However, for a number of reasons, most electrophoresis gels and processes are structured such that the distribution of bases along any given nucleotide-specific lane in the gel and on the resulting autoradiograph is nonlinear over a portion of the gel, such nonlinearity typically being most pronounced in the region of the gel most proximal to the loading well. As is known in the art, this most nonlinear region of the gel proximal to the loading well is sometimes referred to as the "reptation regime." In contrast, the more linear region approaching the end most distal to the loading wells, is sometimes referred to as the "Ogston regime" or "sieving regime."

The substantial nonlinearity in the reptation regime, and, to a lesser extent, in the Ogston regime, results at least in part from the loading process, from thermal diffusion and from gel nonuniformity. More particularly, as a result of these factors, autoradiographs of single-stranded DNA sequences have been observed to have relatively tightly spaced bands at the top end and rather widespread bands at the bottom end. Thus, while it has been relatively easy to read and identify the bases at the extreme bottom end of an autoradiograph, it has been relatively difficult if not impossible to identify the bases approaching the top end of the autoradiograph. This difficulty in identifying bases at the top of the autoradiograph is exacerbated at occurrences of doublets, triplets or other multiple repeated nucleotides as described above.

SUMMARY OF THE INVENTION

In a principal aspect, the present invention takes the form of a computer system comprising a microprocessor and a set of executable instructions, configured to accept a set of input data corresponding to a DNA sequence image from an autoradiograph, and to generate a set of output data substantially identifying or presenting the bases in the DNA sequence in a linear fashion, corresponding to the linear order of nucleotides comprising the DNA sequence, and thereby enabling identification of substantially more bases than could be read by the human eye. In accordance with the invention, the image from the autoradiograph is electronically scanned to create a typically nonlinear set of input data. The set of input data is then analyzed and interpolated in order to establish uniform, linear spacing between the bases in the DNA sequence and in order to facilitate the identification and correction of missing or ambiguously positioned bases.

In an additional embodiment, to be described, enhanced electrophoresis equipment and consumables are also employed in the creation of the autoradiograph that is scanned into the computer system. As a result, the initial set of input data bears increased linearity and predictability, and the interpolative process enables identification of a substantially increased number of bases in the DNA sequence.

Through interpolative processing, as well as the available incorporation of more predictable electrophoresis equipment and consumables, the present invention is thus configured to extract bases from broadened bands and to linearize base positions along substantially the length of the autoradiograph. As a result, the system provides substantially automated means of accurately predicting and extrapolating other band positions along a greater length of the gel, thus resulting in increased numbers of base calls.

It is therefore a primary object of the present invention to provide a system for reading and identifying an increased number of bases in an autoradiograph of a single-stranded DNA sequence.

It is a further object of the present invention to provide a system for enhancing data presentation and enabling longer and more accurate DNA base calls.

Further objects and advantages of the present invention will become apparent in the following description.

DETAILED DESCRIPTION OF THE PREFERRED EMBODIMENTS

Figure 1:
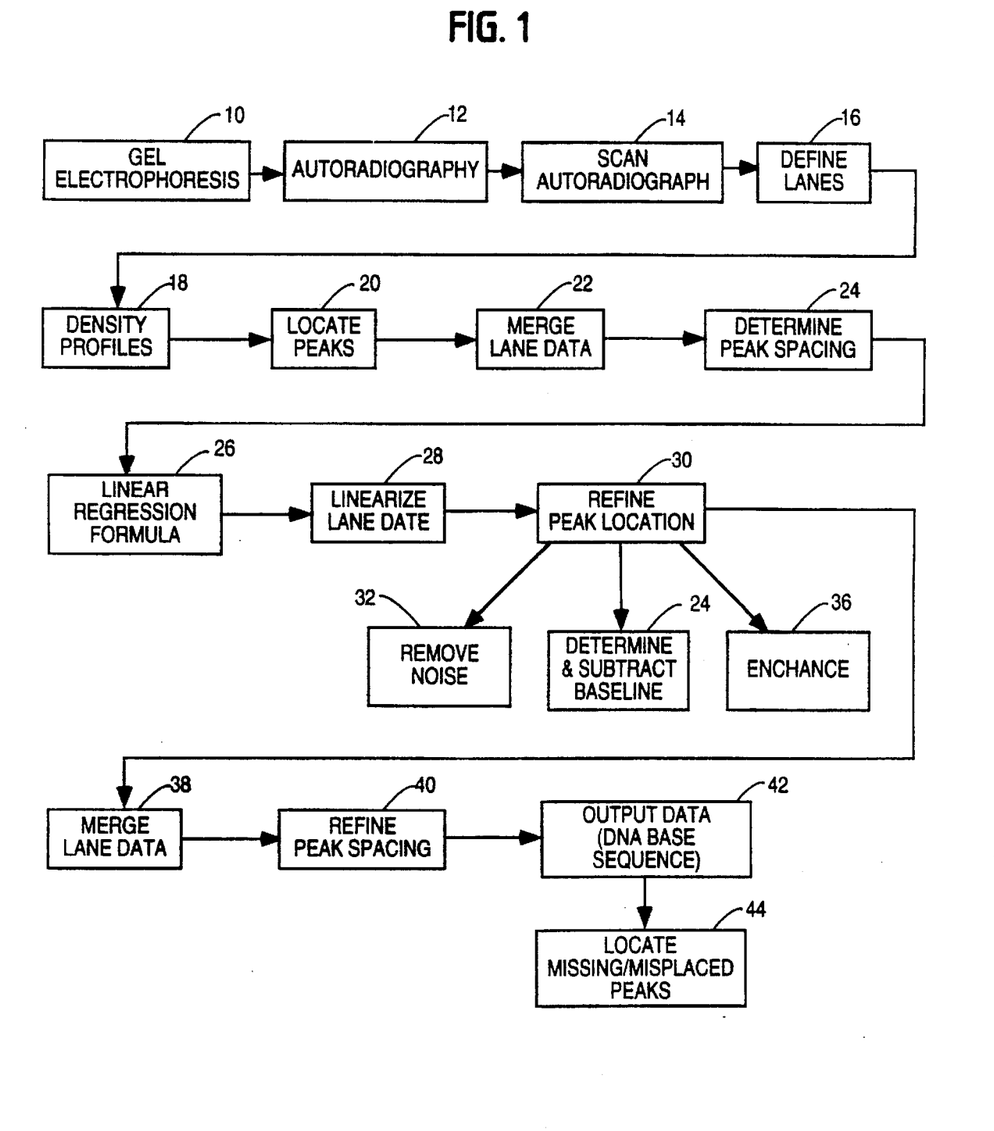
FIG. 1 is a flow chart of the preferred embodiment of the present invention.

The embodiment of the present invention shown in FIG. 1 is a system for analysis of single-stranded nucleic acids, and, more particularly, a system for identification of nucleotides in a single-stranded DNA sequence. With reference to the method steps of the present invention, the embodiment shown in FIG. 1 will now be described.

The present invention provides a system for reading or "calling" nucleotides or "bases" in a DNA sequence. Therefore, a collection of single-stranded DNA fragments is first generated by known processes such as chemical degradation of the nucleic acid or by replacement DNA synthesis using a polymerase. Separate sequencing reactions are then performed for each of the four possible nucleotides (adenine, guanine, cytosine and thymidine). At step 10 of FIG. 1, gel electrophoresis is then performed on each of these four reactions. Typically, the four reactions are electrophoresed in four adjacent lanes of a single sequencing gel.

Figure 2:
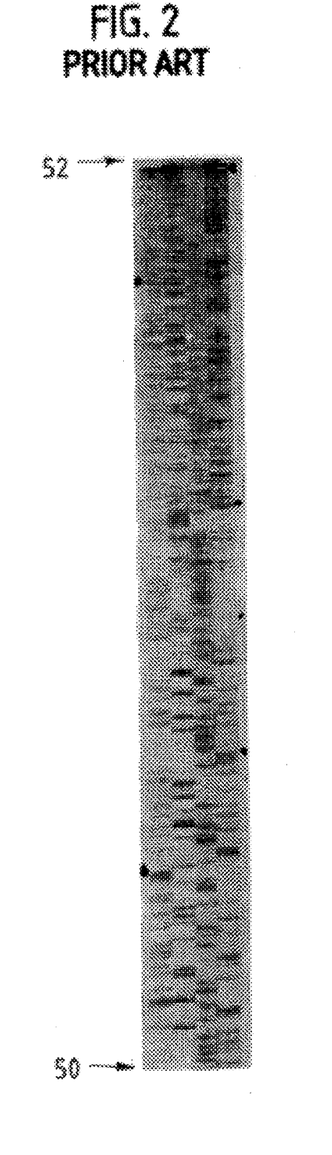
FIG. 2 is an illustration of an autoradiograph image generated with conventional electrophoresis equipment and consumables, prior to processing by the preferred embodiment of the present invention.
Figure 3:
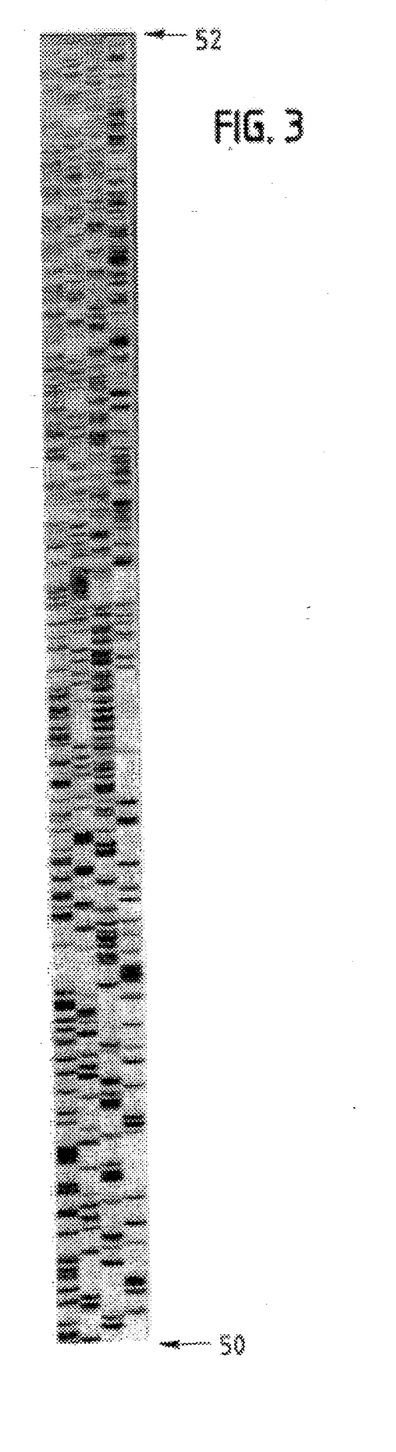
FIG. 3 is an illustration of an autoradiograph image generated with improved electrophoresis equipment and consumables, prior to processing by the preferred embodiment of the present invention.

Assuming that the individual DNA fragments have been radiolabeled, the four adjacent lanes and their respective bands in the gel may then be visualized on an x-ray film by applying autoradiography as indicated at step 12. The resulting x-ray film, or autoradiograph, will thus bear an analog (i.e., non-digital) image of the four adjacent lanes and bands, as generally depicted by FIGS. 2 and 3. As a matter of convention and convenience, the 2B edge or approximate end of the autoradiograph that corresponds to the end of the gel distal to the loading wells will be referred to as the "bottom end." Conversely, the edge or approximate end of the autoradiograph that corresponds to the end of the gel proximal to the loading wells will be referred to as the "top end." Therefore, the "top end" of the autoradiograph may not necessarily coincide with the physical orientation of the autoradiograph under analysis.

The autoradiograph image of FIG. 2 illustrates the results of conventional gel electrophoresis, using conventional electrophoresis equipment and consumables. Notably the bands in each lane approaching the bottom 50 of the autoradiograph are fairly widespread and legible. However, the bands approaching the top 52 of the autoradiograph are substantially compressed, in some cases overlapping, and in some cases unintelligible to the human eye. This standard autoradiograph thus bears a substantially nonlinear distribution of bands along each lane from the bottom end of the autoradiograph to the top end of the autoradiograph, which results at least in part from the loading process, thermal diffusion and gel nonuniformity. Notably, existing gel readers are not capable of materially extending the read of such an autoradiograph beyond the number of bands that could be read by the human eye.

At step 14, the analog image on the autoradiograph is electronically scanned, preferably by a flat bed optical scanner, in order to generate a digital input signal consisting of a set of input data indicative of the analog autoradiograph image. Next, at step 16, the input data is segregated or divided into lane data subsets, each of which is indicative of the analog image of one of the lanes depicted on the autoradiograph. Dividing the data into defined lanes facilitates independent density analysis of the bands in each separate lane. In the preferred embodiment, the lane data subsets should be electronically preserved in memory for use at steps to be subsequently described.

Turning to step 18, each lane data subset is electronically processed, and density profile signals are generated for each lane. Each density profile signal represents the variations of density along the length of a given lane, from the bottom end 50 of the autoradiograph to the top end 52 of the autoradiograph. These density profile signals are then processed, as indicated at step 20, and peak location data subsets are generated for each lane. Each peak location data subset defines the locations of density peaks along each of the lanes with reference to the bottom end of the autoradiograph, where the bands are generally more widely separated and easier to distinguish.

Figure 4:
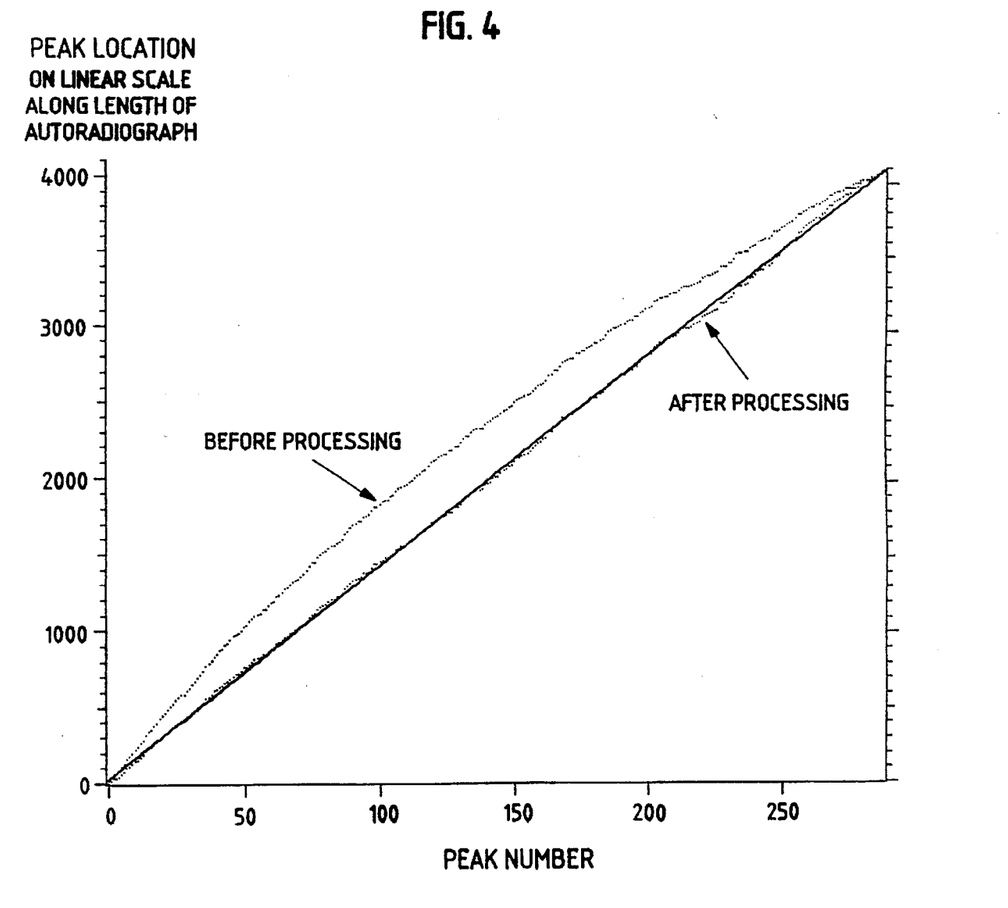
FIG. 4 is a plot of a combined set of peak location data for a given nucleotide sequence.

At step 22, the peak location data subsets for all of the lanes are electronically merged together in order to generate a combined peak location signal. The combined peak location signal represents the combined set of peak location data, which defines the locations of peaks along the length of the autoradiograph for all four lanes combined. As an example, FIG. 4 illustrates a plot of a combined set of peak location data for a given nucleic acid. Notably, due to band broadening as well as the occurrence of multiple repeated nucleotides especially near the top of the autoradiograph, some of the peaks detected in this step may in fact be representative of more than one overlapping band.

In turn, at step 24, the combined peak location signal is electronically processed in order to generate a peak spacing signal representative of a set of peak spacing data. The peak spacing data defines the spacing between peaks along the length of the autoradiograph, with reference to the bottom of the autoradiograph. As illustrated by the curve of FIG. 4, initial peak spacing is generally nonlinear, denoting more widely separated bands near the bottom of the autoradiograph and more closely compressed bands near the top of the autoradiograph.

The present invention next contemplates that, as indicated at step 26, the peak spacing data is electronically interpolated, in order to derive a linearization formula for linearly regressing the nonlinear band distribution (i.e., peak spacing) in each lane. This interpolative linear regression is akin to taking at least a first approximation of a peak location curve such as that shown in FIG. 4. More particularly, the linear regression process seeks to apply the slope of the peak location slope from the bottom (more widespread) portion of each lane to the remainder of each lane, to thereby "stretch" the peak location curve into a curve of substantially constant slope. Phrased alternatively, the linear regression process seeks to redefine the y axis of the peak location vs. peak number curve, so that the points on the curve fall substantially into a line, and so that the Ogston regime is extended and the reptation regime is reduced.

In the preferred embodiment, the interpolative process contemplates the following steps. First, a derivative of the peak location curve is taken, in order to generate a curve indicative of peak spacing. Second, clearly misplaced points on the resulting peak spacing curve ("flier points") are removed, so that single-spaced peak locations remain. Third, the "robust fit" method is used to fit the resulting curve to a straight line. Fourth, the formula for the straight line is integrated, to result in a quadratic equation. The resulting quadratic equation in turn defines the process by which the peak location curve should be modified in order to fit or "stretch" the curve to a line.

Therefore, at step 28, the resulting quadratic equation, or "linearization formula" is applied to each of the lane data subsets (which had been preserved in memory at step 16) in order to generate linearized lane data signals for each lane. Each linearized lane data signal represents linearized peak spacing of density peaks in each of the lanes. More particularly, as a result, the linearized lane data signal for each given lane represents peaks positioned along the given lane such that peak spacing for the four lanes combined is equidistant along the length of the autoradiograph.

Once the existing peaks have been linearly spaced pursuant to step 28, peak analysis and refinement may be performed on the data for each lane. Thus, at step 30, each of the linearized lane data signals is electronically processed so as to generate a refined peak location data subset for each lane. This electronic processing preferably consists of removing noise, at step 32, determining and subtracting a baseline, at step 34, and enhancing the linearized lane data signals, at step 36. More particularly, the step of removing noise contemplates the application of a low-bandpass filter to the given linearized lane data subset in a Fourier Transform domain; the step of determining and subtracting a baseline contemplates the determination of a local minimum across a density profile of the linearized lane data subset as well as the subtraction of excess data fluctuations from the linearized lane data subset; and the step of enhancing consists of emphasizing density peak shoulders throughout the linearized lane data subset. As a result, the refined peak location data subset will include more precise indications of peaks, even in situations of band widening or multiple repeated nucleotides.

Thereafter, at step 38, the refined peak location data subsets for each lane are electronically merged together in order to generate a combined refined peak location signal. The combined refined peak location signal represents a refined set of peak locations along the autoradiograph, combining data from all four nucleotide lanes. In turn, at step 40, the combined refined peak location signal is electronically processed in order to generate a refined peak spacing signal. The refined peak spacing signal represents a refined set of peak spacing data, which defines the spacing between peaks along the autoradiograph with reference to the bottom end of the autoradiograph.

Once the refined peak spacing signal has been generated, the present invention contemplates that misplaced or missing bands along the autoradiograph can be substantially corrected. To this end, at step 42, the linearization formula derived in step 26 is applied to the refined set of peak spacing data. By assuming that every band along the autoradiograph should be equidistantly spaced, this step permits a determination of locations along the autoradiograph where a band should be but is not located, as would be indicated, for instance, by the absence of a band in any lane for at least twice the assumed equidistant space along the autoradiograph. In one embodiment of the present invention, a user may therefor be prompted to manually correct band ambiguities. Any such corrections will modify the refined peak spacing signal.

Finally, at step 44, an output signal is generated. The output signal may consist of a textual display or listing, in which occurrences of each nucleotide are represented by the corresponding letter (e.g., "A", "G", "T" or "C"), and ambiguities may be denoted by another indication such as the letter "N". Alternatively, the output signal may consist of a graphical depiction of the four adjacent nucleotide lanes, substantially illustrating DNA base positions.

Figure 5:
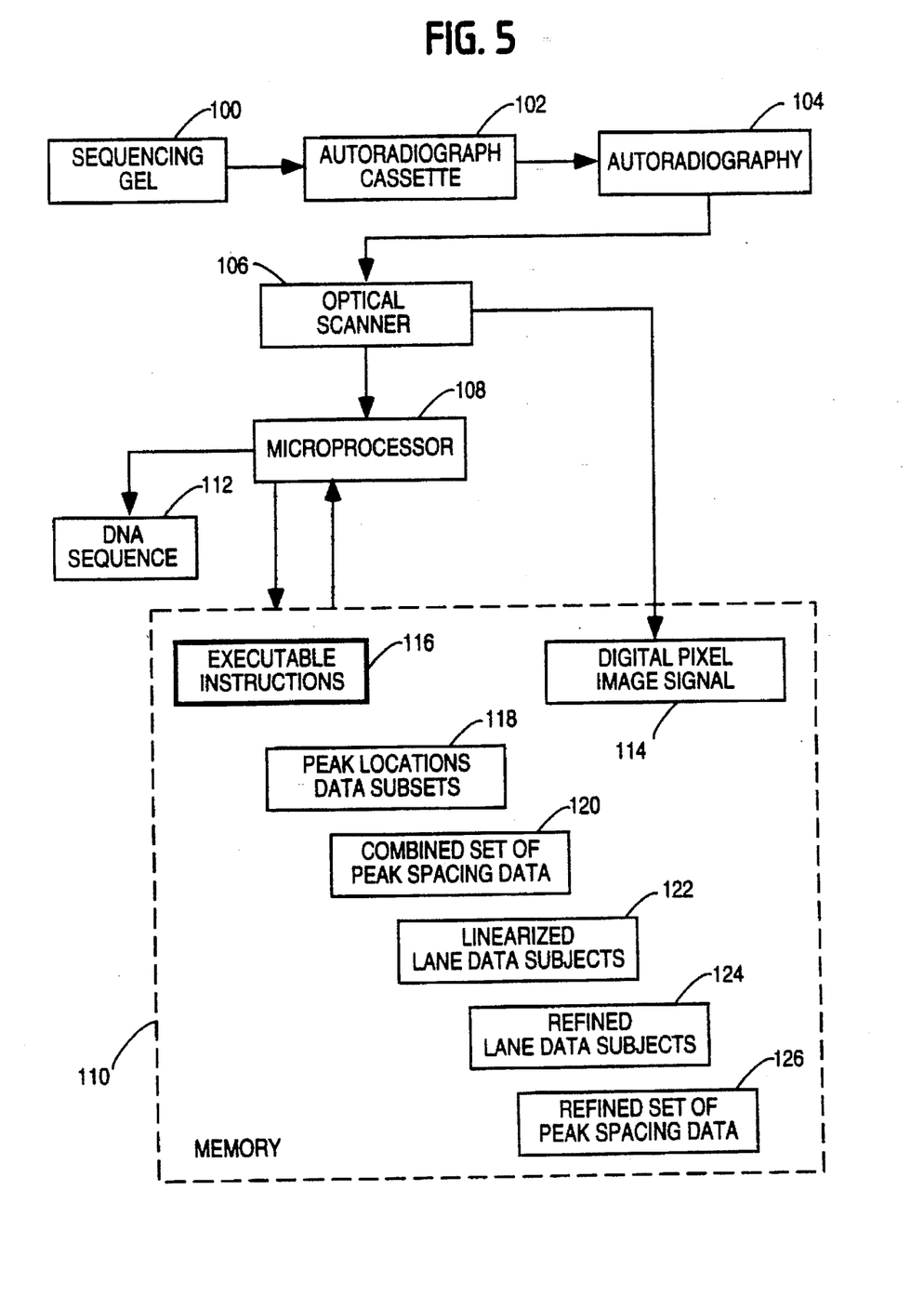
FIG. 5 is a pictorial block diagram of the preferred embodiment of the present invention.

Turning now to FIG. 5, there is shown a pictorial block diagram of the components of the present invention. Structural components of the system include a sequencing gel 100, an autoradiography cassette 102, an autoradiograph 104, a flat bed optical scanner 106, a microprocessor 108, a memory device 110, and a resulting DNA sequence output 112.

As described above, four separate nucleotide-specific reactions are first electrophoresed in substantially adjacent lanes in the sequencing gel 100. As a result, the sequencing gel bears substantially adjacent lanes of spaced bands that substantially indicate the presence of radiolabeled single-stranded DNA molecules of the nucleic acid being analyzed. The sequencing gel 100 is then subjected to an autoradiographic system comprising autoradiograph cassette 102 configured in a manner well known to those skilled in the art to produce an autoradiograph 104. The autoradiograph 104 bears visible image patterns corresponding to the substantially adjacent lanes of bands on the electrophoresed sequencing gel.

The autoradiograph 104 is then scanned by the flat bed optical scanner 106, which, in turn, produces a digital pixel image signal 114 representative of the visible image patterns of the autoradiograph. The optical scanner 106 is interconnected to the microprocessor 108, which enables the scanner to then feed the digital pixel image signal 114 to the memory device 110.

A set of executable instructions 116 operable by the microprocessor is also stored in memory 110. The microprocessor executes these instructions in order to process the digital pixel image signal. First, the microprocessor derives density peaks along each of the lanes of the autoradiograph image, creating a peak location data subset for each lane, and storing these peak location data subsets 118 in the memory 110.

The microprocessor then merges the peak location data subsets 118 together and processes the combined data set so as to generate a combined set of peak spacing data 120, which is then stored in memory. As described above, the combined set of peak spacing data 120 represents the spacing between each of the density peaks along the autoradiograph for the combination of the four nucleotide lanes.

Next, the combined set of peak spacing data is interpolated in order to derive a formula for linearly regressing the peak spacing distribution along the autoradiograph. The microprocessor then applies the linearization formula to the peak location data subsets 118 in order to generate linearized lane data subsets 122, which are, in turn, also stored in memory. By means described above, the microprocessor then processes the linearized lane data subsets 122 in order to emphasize actual density peak locations along the autoradiograph. As a result, the microprocessor generates refined lane data subsets 124 substantially representing the band positions along each of the lanes. The refined lane data subsets 124 are then stored in memory.

Next, the microprocessor merges the refined lane data subsets 124 and processes the combined data subsets in order to generate a refined set of peak spacing data 126, which is stored in memory. The refined set of peak spacing data 126 represents the spacing between band positions along the autoradiograph, taking into consideration the combination of all four lanes of bands.

In one embodiment of the present invention, as described above, the microprocessor next applies the previously-derived linearization formula to the refined set of peak spacing data 126 in order to determine the locations of misplaced and missing bands along the autoradiograph. In this way, such misplaced and missing bands may be appropriately inserted.

Finally, the microprocessor processes the refined set of peak spacing data and generates an DNA sequence output signal 112. As described above at method step 44, the DNA sequence output signal will be indicative of the bases in the DNA sequence for the nucleic acid being analyzed.

It has been observed that the present invention is capable of substantially increasing the number of base calls in a given nucleotide sequence. Still further, it has been observed that application of the above-described computer system in cooperation with improved electrophoresis equipment and consumables will result in an even greater number of base calls for the given sequence.

Examples of beneficial improved electrophoresis equipment and consumables include an air impingement system as described in the '583 application, and a modified or sieving-extending acrylamide sequencing gel, also referred to as a read length extending gel, such as the HR 1000 brand gel produced by Genomyx Corporation. An air impingement system of the type described in the '583 application may be applied to a sequencing gel in order to control temperature during sequencing independent of voltage, and to thereby minimize temperature gradients in the sequencing gel as well as smiling or other effects of such gradients. A sieving-extending acrylamide sequencing gel such as the Genomyx HR 1000 gel improves the linearity of the gel by enlarging the Ogston regime and reducing the reptation regime.

By applying the present invention in conjunction with these improved electrophoresis equipment and consumables, a more linear band distribution results on the autoradiograph to be analyzed. FIG. 3 illustrates the results of gel electrophoresis and autoradiography performed with these improved equipment and consumables. As a result, when the interpolative linear regression is applied at step 28, the underlying first approximation of the peak spacing along the length of this improved autoradiograph will more likely and more easily reach a constant slope. In turn, more DNA bases will be identified.

MICROPROCESSOR PROGRAMMING

The executable instructions 116 stored in the computer memory 110 are assembled from the instructions shown in the source code listing that appears at the conclusion of this specification. The microprocessor 108 for executing the instructions 116 should be a Motorola 68020 microprocessor or a more advanced yet compatible microprocessor, such as can be found on a Macintosh running at least 7.1 system software. Macintosh Programmers Workshop (MPW) version 3.3.1 should be used to compile these instructions. At least 6 Megabytes of RAM (read only memory) must be available to run this sequencing software. Furthermore, the memory 110 must be set for 32 bit addressing. A monitor of at least 13 inches is strongly recommended, and the monitor must be set for 256 colors. For the fastest runtime, a floating point option on a math chip is required. Finally, the flat bed optical scanner 106 must be set for 600 dots per inch, gray scale and reflective mode, to enable reading of an image from the autoradiograph x-ray film.

The instructions listed below are divided into subprograms or functions, including, but not limited to, the following functions:

| Function Name | Purpose of Function |
| --- | --- |
| DoEngine | The driving or main function for the entire software system or "engine." |
| SetEngineParams | Sets the initial value for the engine parameters. These parameters control the behavior of each part of the engine. |
| Stretch | Finds the peaks, finds the peak spacing, fits the peak spacing, stretches the data so that the peak spacing is constant. |
| DiddleParams | Adjusts the engine parameters based on the peak spacing value obtained by the Stretch function. |
| PrefsToParams | Further adjusts the engine parameters based on manually set preferences. |
| RemoveNoise | Removes high frequency noise from data using a Fast Fourier Transform with a cut-off filter. |
| CalcBaseline | Calculates a baseline using data minima. |
| RemoveBaseline | Subtracts baseline from the data. |
| Enhance | Enhances the data. |
| ScaleData8Segs | Scales the data to equalize peak heights throughout the data range. |
| FindPeaks | Finds the peaks using a top-hat filtering and threshold detection. |
| SetOutputLanes | Copies data profiles into an array for display on a video terminal. |
| DoZipper | Fits the peak spacing, inserts peaks where the space is sufficiently wider than the space expected based on the fit. |
| UnStretchBool | Unstretch peak positions (both those found by FindPeaks and those inserted by DoZipper) for display on the video terminal. |
| DoTextCall | Constructs a base call comprising a set of letters (A, C, G, T and N) based on the peaks (both those found and those inserted). |

As indicated above, the preferred embodiment of the invention has been implemented using programs compiled for execution on the Macintosh family of computers manufactured by Apple Computer, Inc., 20525 Mariani Avenue, Cupertino, Calif. The programs include were written, in part, in the C and Pascal languages. These programs were compiled using standard compilers available from Apple Computer, Inc., such as the Macintosh Programmers Workshop version 3.3.1. The source language listings for these programs are listed below, with the assembly language programs being presented first, followed by the C language header listings, the C language listings, and concluding with the Pascal listings.

| Assembly Language Listings: | |
| --- | --- |
| !CARDHAN | A |
| !CARDSTU | A |
| !SIGNAL_ | A |

| C Language Header Listings | |
| --- | --- |
| !EDITBAS | H |
| !FINDPEA | H |
| !PALETTE | H |
| !REMOVEN | H |
| BASELINE | H |
| ENGINE | H |
| LAYERS | H |
| NRUTIL | H |
| STRETCH | H |
| TEMPLATE | H |
| TIFF | H |
| ZIPPER | H |
| C Language Listings | |
| !FINDPEA | C |
| !FLOATCO | C |
| !PALETTE | C |
| !REMOVEN | C |
| BASELINE | C |
| C_MATH | C |
| ENGINE | C |
| GAUSS | C |
| STRETCH | C |
| TEMPLATE | C |
| TIFF | C |
| ZIPPER | C |
| Pascal Language Listings | |
| !AMBIGUI | P |
| !CAMERA2 | P |
| !CAMERA_ | P |
| !COORDIN | P |
| !EDITBAS | P |
| !FLOATCO | P |
| !MANUAL_ | P |
| !MATH_TO | P |
| !MULTI_G | P |
| !PALETTE | P |
| !RANGE_S | P |
| !SEQUENC | P |
| !SEQ_GLO | P |
| !STANDAR | P |
| ENGINE | P |
| HOMOLOGY | P |
| MATH_1D | P |
| MOL_WT | P |
| TEMPLATE | P |
| TIFF | P |

Each of these source code files follows:

While a preferred embodiment of the present invention has been depicted and described, it will be appreciated by those skilled in the art that many modifications, substitutions and changes may be made thereto without departing from the true spirit and scope of the invention.

We claim:

1. A method for identifying nucleotides in a sequence of nucleotides comprising a nucleic acid, said method comprising:

conducting gel electrophoresis on a plurality of radiolabeled single-stranded DNA fragments derived from said nucleic acid, said gel electrophoresis being conducted in a sequencing gel and including application of an air impingement system to control temperature during sequencing independent of voltage, and thereby to minimize temperature gradients in said sequencing gel;

generating an autoradiograph of said sequencing gel, said autoradiograph thereby bearing an analog image comprising a plurality of adjacent lanes extending from a bottom end of said autoradigraph to a top end of said autoradiograph;

scanning said autoradiograph to generate an input signal consisting of a set of input data indicative of said analog image;

electronically segregating said input data into lane data subsets corresponding to each of said adjacent lanes;

processing each of said land data subsets to generate respective density profile signals representative of density variations along each of said adjacent lanes from said bottom end of said autoradiograph to said top end of said autoradiograph;

electronically generating a peak location data subset for each of said lanes, responsive to each of said respective density profile signals, each said peak location data subset defining locations of density peaks along each of said lanes with reference to said bottom end of said autoradiograph;

merging together said peak location data subsets for each of said lanes so as to generate combined peak location signal representative of a combined set of peak location data;

generating, responsive to said combined peak location signal, a peak spacing signal representative of a set of peak spacing data defining peak spacing along said autoradiograph with reference to said bottom end of said autoradiograph;

electronically interpolating said peak spacing data so as to generate a linearization formula for spacing of peaks along said autoradiograph;

applying said linearization formula to each of said lane data subsets so as to generate linearized lane data signals corresponding to linearized peak spacing of density peaks in each of said lanes;

electronically generating a refined peak location data subset for each of said lanes, by subjecting each of said linearized lane data signals to method steps comprising:
removing noise;
determining and subtracting a baseline; and
emphasizing density peak shoulders;

merging together said refined peak location data subsets for each of said lanes so as to generate a combined refined peak location signal representative of a combined refined set of peak location data;

generating, responsive to said combined refined peak location signal, a refined peak spacing signal representative of a refined set of peak spacing data, defining peak spacing along said autoradiograph with reference to said bottom end of said autoradiograph;

electronically applying said linearization formula to said refined set of peak spacing data so as to determine locations of misplaced and missing peaks along said autoradiograph and to enable appropriate insertion of said misplaced and missing peaks; and generating an output signal corresponding to said plurality of lanes bearing said linearized spacing of peaks, said peaks corresponding to bases in said DNA sequence.

2. A method for identifying nucleotides in a sequence of nucleotides comprising a nucleic acid, said method comprising:

conducting gel electrophoresis on a plurality of radiolabeled single-stranded DNA fragments derived from said nucleic acid, said gel electrophoresis being conducted in a sequencing gel comprising a read length extending acrylamide;

generating an autoradiograph of said sequencing gel, said autoradiograph thereby bearing an analog image comprising a plurality of adjacent lanes extending from a bottom end of said autoradiograph to a top end of said autoradiograph;

scanning said autoradiograph to generate an input signal consisting of a set of input data indicative of said analog image;

electronically segregating said input data into lane data subsets corresponding to each of said adjacent lanes;

processing each of said lane data subsets to generate respective density profile signals representative of density variations along each of said adjacent lanes from said bottom end of said autoradiograph to said top end of said autoradiograph;

electronically generating a peak location data subset for each of said lanes, responsive to each of said respective density profile signals, each said peak location data subset defining locations of density peaks along each of said lanes with reference to said bottom end of said autoradiograph;

merging together said peak location data subsets for each of said lanes so as to generate a combined peak location signal representative of a combined set of peak location data;

generating, responsive to said combined peak location signal, a peak spacing signal representative of a set of peak spacing data defining peak spacing along said autoradiograph with reference to said bottom end of said autoradiograph;

electronically interpolating said peak spacing data so as to generate a linearization formula for spacing of peaks along said autoradiograph;

applying said linearization formula to each of said lane data subsets so as to generate linearized lane data signals corresponding to linearized peak spacing of density peaks in each of said lanes;

electronically generating a refined peak location data subset for each of said lanes, by subjecting each of said linearized lane data signals to method steps comprising:
removing noise;
determining and subtracting a baseline; and
emphasizing density peak shoulders;

merging together said refined peak location data subsets for each of said lanes so as to generate a combined refined peak location signal representative of a combined refined set of peak location data;

generating, responsive to said combined refined peak location signal, a refined peak spacing signal representative of a refined set of peak spacing data, defining peak spacing along said autoradiograph with reference to said bottom end of said autoradiograph;

electronically applying said linearization formula to said refined set of peak spacing data so as to determine locations of misplaced and missing peaks along said autoradiograph and to enable appropriate insertion of said misplaced and missing peaks; and generating an output signal corresponding to said plurality of lanes bearing said linearized spacing of peaks, said peaks corresponding to bases in said DNA sequence.

3. A method as claimed in claim 2 wherein said read length extending acrylamide comprises Genomyx HR 1000 brand high resolution gel.

4. A method for calling bases from an autoradiograph of a DNA nucleotide sequence, said autoradiograph being generated by gel electrophoresis and bearing an analog image comprising a plurality of adjacent lanes extending from a bottom end of said autoradiograph to a top end of said autoradiograph, said method comprising, in combination, the following steps:

(a) scanning said autoradiograph to generate input data indicative of said analog image;

(b) segregating said input data into lane data subsets corresponding to each of said adjacent lanes;

(c) processing each of said lane data subsets to generate a density profile along each of said adjacent lanes from said bottom end of said autoradiograph to said top end of said autoradiograph;

(d) generating a peak location data subset for each of said lanes based on said density profile along said lane, each said peak location data subset defining locations of density peaks along each of said lanes with reference to said bottom end of said autoradiograph;

(e) merging together said peak location data subsets for each of said lanes so as to generate a combined set of peak location data;

(f) generating, from said combined set of peak location data, a set of peak spacing data defining peak spacing along said autoradiograph with reference to said bottom end of said autoradiograph;

(g) applying interpolative linear regression to said peak spacing data so as to generate a linearization formula for spacing of peaks along said autoradiograph;

(h) applying said linearization formula to each of said lane data subsets so as to generate linearized lane data subsets corresponding to linearized peak spacing of density peaks in each of said lanes;

(i) generating a refined peak location data subset for each of said lanes, by subjecting each of said linearized lane data subsets to method steps comprising (A) removing noise, (B) determining and subtracting a baseline and (C) emphasizing density peak shoulders, wherein said step of removing noise comprises applying a low-bandpass filter to each of said linearized lane data subsets in a Fourier Transform Domain;

(j) merging together said refined peak location data subsets for each of said lanes so as to generate a combined refined set of peak location data;

(k) generating, from said combined refined set of peak location data, a refined set of peak spacing data defining peak spacing along said autoradiograph with reference to said bottom end of said autoradiograph;

(l) applying said linearization formula to said refined set of peak spacing data so as to determine locations of misplaced and missing peaks along said autoradiograph and to enable appropriate insertion of said misplaced and missing peaks; and (m) generating a set of output data corresponding to said plurality of lanes bearing said linearized spacing of peaks, said peaks corresponding to bases in said DNA sequence.

5. A method for calling bases from an autoradiograph of a DNA nucleotide sequence, said autoradiograph being generated by gel electrophoresis and bearing an analog image comprising a plurality of adjacent lanes extending from a bottom end of said autoradiograph to a top end of said autoradiograph, said method comprising, in combination, the following steps:

(a) scanning said autoradiograph to generate input data indicative of said analog image;

(b) segregating said input data into lane data subsets corresponding to each of said adjacent lanes;

(c) processing each of said lane data subsets to generate a density profile along each of said adjacent lanes from said bottom end of said autoradiograph to said top end of said autoradiograph;

(d) generating a peak location data subset for each of said lanes based on said density profile along said lane, each said peak location data subset defining locations of density peaks along each of said lanes with reference to said bottom end of said autoradiograph;

(e) merging together said peak location data subsets for each of said lanes so as to generate a combined set of peak location data;

(f) generating, from said combined set of peak location data, a set of peak spacing data defining peak spacing along said autoradiograph with reference to said bottom end of said autoradiograph;

(g) applying interpolative linear regression to said peak spacing data so as to generate a linearization formula for spacing of peaks along said autoradiograph;

(h) applying said linearization formula to each of said lane data subsets so as to generate linearized lane data subsets corresponding to linearized peak spacing of density peaks in each of said lanes;

(i) generating a refined peak location data subset for each of said lanes, by subjecting each of said linearized lane data subsets to method steps comprising (A) removing noise, (B) determining and subtracting a baseline and (C) emphasizing density peak shoulders, wherein said step of determining and subtracting a baseline comprises determining a local minimum across a density profile of said linearized lane data subset and subtracting excess data fluctuations from said linearized lane data subset;

(j) merging together said refined peak location data subsets for each of said lanes so as to generate a combined refined set of peak location data;

(k) generating, from said combined refined set of peak location data, a refined set of peak spacing data defining peak spacing along said autoradiograph with reference to said bottom end of said autoradiograph;

(l) applying said linearization formula to said refined set of peak spacing data so as to determine locations of misplaced and missing peaks along said autoradiograph and to enable appropriate insertion of said misplaced and missing peaks; and (m) generating a set of output data corresponding to said plurality of lanes bearing said linearized spacing of peaks, said peaks corresponding to bases in said DNA sequence.

6. A program storage device readable by a machine, tangibly embodying a program of instructions for calling bases from an autoradiograph of a DNA nucleotide sequence, said autoradiograph being generated by gel electrophoresis and bearing an analog image comprising a plurality of adjacent lanes extending from a bottom end of said autoradiograph to a top end of said autoradiograph, said analog image defining input data, said program of instructions being executable by the machine to perform method steps comprising, in combination:

(a) segregating said input data into lane data subsets corresponding to each of said adjacent lanes;

(b) processing each of said lane data subsets to generate a density profile along each of said adjacent lanes from said bottom end of said autoradiograph to said top end of said autoradiograph;

(c) generating a peak location data subset for each of said lanes based on said density profile along said lane, each said peak location data subset defining locations of density peaks along each of said lanes with reference to said bottom end of said autoradiograph;

(d) merging together said peak location data subsets for each of said lanes so as to generate a combined set of peak location data;

(e) generating, from said combined set of peak location data, a set of peak spacing data defining peak spacing along said autoradiograph with reference to said bottom end of said autoradiograph;

(f) applying interpolative linear regression to said peak spacing data so as to generate a linearization formula for spacing of peaks along said autoradiograph;

(g) applying said linearization formula to each of said lane data subsets so as to generate linearized lane data subsets corresponding to linearized peak spacing of density peaks in each of said lanes;

(h) generating a refined peak location data subset for each of said lanes, by subjecting each of said linearized lane data subsets to method steps comprising:
removing noise;
determining and subtracting a baseline; and
enhancing;

(i) merging together said refined peak location data subsets for each of said lanes so as to generate a combined refined set of peak location data;

(j) generating, from said combined refined set of peak location data, a refined set of peak spacing data defining peak spacing along said autoradiograph with reference to said bottom end of said autoradiograph;

(k) applying said linearization formula to said refined set of peak spacing data so as to determine locations of misplaced and missing peaks along said autoradiograph and to enable appropriate insertion of said misplaced and missing peaks; and (l) generating a set of output data corresponding to said plurality of lanes bearing said linearized spacing of peaks, said peaks corresponding to bases in said DNA sequence.

7. An apparatus for producing output data indicative of nucleotide bases in a DNA sequence of a nucleic acid, said apparatus comprising, in combination:

(a) an electrophoresis system for producing an electrophoresed sequencing gel bearing adjacent lanes of spaced bands substantially indicative of radiolabeled single-stranded DNA molecules of said nucleic acid;

(b) an autoradiographic system for producing an autoradiograph bearing an image of said electrophoresed sequencing gel, said image comprising adjacent lanes of visible image patterns extending substantially from a bottom end of said autoradiograph to a top end of said autoradiograph;

(c) an optical scanner for producing a digital pixel image signal representative of said visible image patterns;

(d) a memory for storing data values; and (e) processing means coupled to said optical scanner and to said memory comprising, in combination:
(6) a microprocessor;
(ii) density derivation means coupled to said microprocessor and to said memory, for processing said digital pixel image signal to derive peak location data subsets corresponding to density peaks along each of said lanes, said peak location data subsets being stored in said memory;

(iii) spacing determination means coupled to said microprocessor and to said memory, for merging said peak location data subsets together into a first merged data set and for processing said first merged data set to generate a combined set of peak spacing data corresponding to spacing between each of said density peaks along said autoradiograph for all of said lanes combined, said combined set of peak spacing data being stored in said memory;

(iv) interpolation means coupled to said microprocessor and to said memory, for interpolating said combined set of peak spacing data to derive a linearizing formula for linearizing each of said peak location data subsets;

(v) linear spacing means coupled to said microprocessor and to said memory, for applying said linearizing formula to each of said peak location data subsets so as to generate linearized lane data subsets corresponding to linearized spacing of density peaks in each of said lanes, said linearized lane data subsets being stored in said memory;

(vi) peak refining means coupled to said microprocessor and to said memory, for emphasizing density peaks represented by each of said linearized lane data subsets so as to generate refined lane data subsets corresponding substantially to said band positions along each of said lanes, said refined lane data subsets being stored in said memory;

(vii) refined spacing determination means coupled to said microprocessor and to said memory, for merging said refined lane data subsets together into a second merged data set and for processing said second merged data set to generate a refined set of peak spacing data corresponding to spacing between each of said band positions along said autoradiograph for all of said lanes combined, said refined set of peak spacing data being stored in said memory;

(viii) band replacement means coupled to said microprocessor and to said memory, for applying said linearizing formula to said refined set of peak spacing data so as to determine locations of misplaced and missing bands along said autoradiograph and to enable insertion into additional data points into said refined set of peak spacing data, said additional data points being indicative of appropriate placement of said misplaced and missing bands; and (ix) sequence generating means for processing said refined set of peak spacing data and for generating an output signal corresponding substantially to said nucleotide bases in said DNA sequence.

8. An apparatus for producing output data indicative of nucleotide bases in a DNA sequence of a nucleic acid, said apparatus comprising, in combination:

(a) an electrophoresis system for producing an electrophoresed sequencing gel bearing adjacent lanes of spaced bands substantially indicative of radiolabeled single-stranded DNA molecules of said nucleic acid;

(b) an air impingement system for controlling temperature during sequencing independent of voltage and for minimizing temperature gradients in said sequencing gel;

(c) an autoradiographic system for producing an autoradiograph bearing an image of said electrophoresed sequencing gel, said image comprising adjacent lanes of visible image patterns extending substantially from a bottom end of said autoradiograph to a top end of said autoradiograph;

(d) an optical scanner for producing a digital pixel image signal representative of said visible image patterns;

(e) a memory for storing data values; and
(f) processing means coupled to said optical scanner and to said memory comprising, in combination:
  (i) a microprocessor;
  (ii) density derivation means coupled to said microprocessor and to said memory, for processing said digital pixel image signal to derive peak location data subsets corresponding to density peaks along each of said lanes, said peak location data subsets being stored in said memory;
  (iii) spacing determination means coupled to said microprocessor and to said memory, for merging said peak location data subsets together into a first merged data set and for processing said first merged data set to generate a combined set of peak spacing data corresponding to spacing between each of said density peaks along said autoradiograph for all of said lanes combined, said combined set of peak spacing data being stored in said memory;
  (iv) interpolation means coupled to said microprocessor and to said memory, for interpolating said combined set of peak spacing data to derive a linearizing formula for linearizing each of said peak location data subsets;
  (v) linear spacing means coupled to said microprocessor and to said memory, for applying said linearizing formula to each of said peak location data subsets so as to generate linearized lane data subsets corresponding to linearized spacing of density peaks in each of said lanes, said linearized lane data subsets being stored in said memory;
  (vi) peak refining means coupled to said microprocessor and to said memory, for emphasizing density peaks represented by each of said linearized lane data subsets so as to generate refined lane data subsets corresponding substantially to said band positions along each of said lanes, said refined lane data subsets being stored in said memory;
  (vii) refined spacing determination means coupled to said microprocessor and to said memory, for merging said refined lane data subsets together into a second merged data set and for processing said second merged data set to generate a refined set of peak spacing data corresponding to spacing between each of said band positions along said autoradiograph for all of said lanes combined, said refined set of peak spacing data being stored in said memory; and
  (viii) sequence generating means for processing said refined set of peak spacing data and for generating an output signal corresponding substantially to said nucleotide bases in said DNA sequence.

9. An apparatus for producing output data indicative of nucleotide bases in a DNA sequence of a nucleic acid, said apparatus comprising, in combination:
  (a) an electrophoresis system for producing an electrophoresed sequencing gel bearing adjacent lanes of spaced bands substantially indicative of radiolabeled single-stranded DNA molecules of said nucleic acid, said sequencing gel comprising a read length extending acrylamide;
  (b) an autoradiographic system for producing an autoradiograph bearing an image of said electrophoresed sequencing gel, said image comprising adjacent lanes of visible image patterns extending substantially from a bottom end of said autoradiograph to a top end of said autoradiograph;
  (c) an optical scanner for producing a digital pixel image signal representative of said visible image patterns;
  (d) a memory for storing data values;
  (e) processing means couple to said optical scanner and to said memory comprising, in combination:
    (i) a microprocessor;
    (ii) density derivation means coupled to said microprocessor and to said memory, for processing said digital pixel image signal to derive peak location data subsets corresponding to density peaks along each of said lanes, said peak location data subsets being stored in said memory;
    (iii) spacing determination means coupled to said microprocessor and to said memory, for merging said peak location data subsets together into a first merged data set and for processing said first merged data set to generate a combined set of peak spacing data corresponding to spacing between each of said density peaks along said autoradiograph for all of said lanes combined, said combined set of peak spacing data being stored in said memory;
    (iv) interpolation means coupled to said microprocessor and to said memory, for interpolating said combined set of peak spacing data to derive a linearizing formula for linearizing each of said peak location data subsets;
    (v) linear spacing means coupled to said microprocessor and to said memory, for applying said linearizing formula to each of said peak location data subsets so as to generate linearized lane data subsets corresponding to linearized spacing of density peaks in each of said lanes, said linearized lane data subsets being stored in said memory;
    (vi) peak refining means coupled to said microprocessor and to said memory, for emphasizing density peaks represented by each of said linearized lane data subsets so as to generate refined lane data subsets corresponding substantially to said band positions along each of said lanes, said refined lane data subsets being stored in said memory;
    (vii) refined spacing determination means coupled to said microprocessor and to said memory, for merging said refined lane data subsets together into a second merged data set and for processing said second merged data set to generate a refined set of peak spacing data corresponding to spacing between each of said band positions along said autoradiograph for all of said lanes combined, said refined set of peak spacing data being stored in said memory; and
    (viii) sequence generating means for processing said refined set of peak spacing data and for generating an output signal corresponding substantially to said nucleotide bases in said DNA sequence.

10. An apparatus as claimed in claim 9 wherein said read length extending acrylamide comprises Genomyx HR 1000 brand high resolution gel.

11. An apparatus for producing output data indicative of nucleotide bases in a DNA sequence of a nucleic acid, said apparatus comprising, in combination:
  (a) an electrophoresis system for producing an electrophoresed sequencing gel bearing adjacent lanes of spaced bands substantially indicative of radiolabeled single-stranded DNA molecules of said nucleic acid;
  (b) an autoradiographic system for producing an autoradiograph bearing an image of said electrophoresed sequencing gel, said image comprising adjacent lanes of visible image patterns extending substantially from a bottom end of said autoradiograph to a top end of said autoradiograph;

(c) an optical scanner for producing a digital pixel image signal representative of said visible image patterns;

(d) a memory for storing data values;

(e) processing means coupled to said optical scanner memory comprising, in combination a microprocessor and a set of instructions executable by microprocessor, said set of instructions comprising, in combination:

(i) density derivation means coupled to said microprocessor and to said memory, for processing said digital pixel image signal to derive peak location data subsets corresponding to density peaks along each of said lanes, said peak location data subsets being stored in said memory;

(ii) spacing determination means coupled to said microprocessor and to said memory, for merging said peak location data subsets together into a first merged data set and for processing said first merged data set to generate a combined set of peak spacing data corresponding to spacing between each of said density peaks along said autoradiograph for all of said lanes combined, said combined set of peak spacing data being stored in said memory;

(iii) interpolation means coupled to said microprocessor and to said memory, for interpolating said combined set of peak spacing data to derive a linearizing formula for linearizing each of said peak location data subsets;

(iv) linear spacing means coupled to said microprocessor and to said memory, for applying said linearizing formula to each of said peak location data subsets so as to generate linearized lane data subsets corresponding to linearized spacing of density peaks in each of said lanes, said linearized lane data subsets being stored in said memory;

(v) peak refining means coupled to said microprocessor and to said memory, for emphasizing density peaks represented by each of said linearized lane data subsets so as to generate refined lane data subsets corresponding substantially to said band positions along each of said lanes, said refined lane data subsets being stored in said memory;

(vi) refined spacing determination means coupled to said microprocessor and to said memory, for merging said refined lane data subsets together into a second merged data set and for processing said second merged data set to generate a refined set of peak spacing data corresponding to spacing between each of said band positions along said autoradiograph for all of said lanes combined, said refined set of peak spacing data being stored in said memory; and (vii) sequence generating means for processing said refined set of peak spacing data and for generating an output signal corresponding substantially to said nucleotide bases in said DNA sequence.

12. An apparatus as claimed in claim 11 wherein said instructions are stored in said memory.

13. An apparatus for producing output data indicative of nucleotide bases in a DNA sequence of a nucleic acid, said apparatus comprising, in combination:

(a) an electrophoresis system for producing an electrophoresed sequencing gel bearing adjacent lanes of spaced bands substantially indicative of radiolabeled single-stranded DNA molecules of said nucleic acid;

(b) an autoradiographic system for producing an autoradiograph bearing an image of said electrophoresed sequencing gel, said image comprising adjacent lanes of visible image patterns extending substantially from a bottom end of said autoradiograph to a top end of said autoradiograph;

(c) an optical scanner for producing a digital pixel image signal representative of said visible image patterns;

(d) a memory for storing data values;

(e) processing means coupled to said optical scanner and to said memory comprising, in combination:

(i) a microprocessor;

(ii) density derivation means coupled to said microprocessor and to said memory, for processing said digital pixel image signal to derive peak location data subsets corresponding to density peaks along each of said lanes, said peak location data subsets being stored in said memory;

(iii) spacing determination means coupled to said microprocessor and to said memory, for merging said peak location data subsets together into a first merged data set and for processing said first merged data set to generate a combined set of peak spacing data corresponding to spacing between each of said density peaks along said autoradiograph for all of said lanes combined, said combined set of peak spacing data being stored in said memory;

(iv) interpolation means coupled to said microprocessor and to said memory, for interpolating said combined set of peak spacing data to derive a linearizing formula for linearizing each of said peak location data subsets;

(v) linear spacing means coupled to said microprocessor and to said memory, for applying said linearizing formula to each of said peak location data subsets so as to generate linearized lane data subsets corresponding to linearized spacing of density peaks in each of said lanes, said linearized lane data subsets being stored in said memory;

(vi) peak refining means coupled to said microprocessor and to said memory, for emphasizing density peaks represented by each of said linearized lane data subsets so as to generate refined lane data subsets corresponding substantially to said band positions along each of said lanes, said refined lane data subsets being stored in said memory, said peak refining means further comprising, in combination:

noise removal means;

baseline means comprising (A) means for determining a local minimum across a density profile of each of said linearized lane data subsets and (B) means for subtracting excess data fluctuations from each of said linearized lane data subsets; and enhancement means;

(vii) refined spacing determination means coupled to said microprocessor and to said memory, for merging said refined lane data subsets together into a second merged data set and for processing said second merged data set to generate a refined set of peak spacing data corresponding to spacing between each of said band positions along said autoradiograph for all of said lanes combined, said refined set of peak spacing data being stored in said memory; and (viii) sequence generating means for processing said refined set of peak spacing data and for generating an output signal corresponding substantially to said nucleotide bases in said DNA sequence.

14. An apparatus as claimed in claim 13 wherein said noise removal means comprises means for applying a low-bandpass filter to each of said linearized lane data subsets in a Fourier Transform domain.

15. An apparatus as claimed in claim 13 wherein said enhancement means comprises means for enhancing density peak shoulders throughout each of said linearized lane data subsets.

16. A system for identifying nucleotides in a sequence of nucleotides conprising a nucleic acid, said system comprising, in combination:

means for conducting gel electrophoresis on a plurality of radiolabeled single-stranded DNA fragments derived from said nucleic acid, said gel electrophoresis being conducted in a sequencing gel, said means for conducting gel electrophoresis including means for applying an air impingement system to control temperature during sequencing independent of voltage, and thereby to minimize temperature gradients in said sequencing gel;

means for generating an autoradiograph of said sequencing gel, said autoradiograph thereby bearing an analog image comprising a plurality of adjacent lanes extending from a bottom end of said autoradiograph to a top end of said autoradiograph;

means for scanning said autoradiograph to generate input data indicative of said analog image;

means for segregating said input data into lane data subsets corresponding to each of said adjacent lanes;

means for processing each of said lane data subsets to generate a density profile along each of said adjacent lanes from said bottom end of said autoradiograph to said top end of said autoradiograph;

means for generating a peak location data subset for each of said lanes based on said density profile along said lane, each said peak location data subset defining locations of density peaks along each of said lanes with reference to said bottom end of said autoradiograph;

means for merging together said peak location data subsets for each of said lanes so as to generate a combined set of peak location data;

means for generating, from said combined set of peak location data, a set of peak spacing data defining peak spacing along said autoradiograph with reference to said bottom end of said autoradiograph;

means for applying interpolative linear regression to said peak spacing data so as to generate a linearization formula for spacing of peaks along said autoradiograph;

means for applying said linearization formula to each of said lane data subsets so as to generate linearized lane data subsets corresponding to linearized peak spacing of density peaks in each of said lanes;

means for generating a refined peak location data subset for each of said lanes, comprising:

(i) means for removing noise from each of said linearized lane data subsets;

(ii) means for determining and subtracting a baseline from each of said linearized lane data subsets;

(iii) means for enhancing each of said linearized lane data subsets;

means for merging together said refined peak location data subsets for each of said lanes so as to generate a combined refined set of peak location data;

means for generating, from said combined refined set of peak location data, a refined set of peak spacing data defining peak spacing along said autoradiograph with reference to said bottom end of said autoradiograph;

means for applying said linearization formula to said refined set of peak spacing data so as to determine locations of misplaced and missing peaks along said autoradiograph and to enable appropriate insertion of said misplaced and missing peaks; and     means for generating a set of output data corresponding to said plurality of lanes bearing said linearized spacing of peaks, said peaks corresponding to bases in said DNA sequence.

17. A system for identifying nucleotides in a sequence of nucleotides comprising a nucleic acid, said system comprising, in combination:

means for conducting gel electrophoresis on a plurality of radiolabeled single-stranded DNA fragments derived from said nucleic acid, said gel electrophoresis being conducted in a sequencing gel comprising a read length extending acrylamide;

means for generating an autoradiograph of said sequencing gel, said autoradiograph thereby bearing an analog image comprising a plurality of adjacent lanes extending from a bottom end of said autoradiograph to a top end of said autoradiograph;

means for scanning said autoradiograph to generate input data indicative of said analog image;

means for segregating said input data into lane data subsets corresponding to each of said adjacent lanes;

means for processing each of said lane data subsets to generate a density profile along each of said adjacent lanes from said bottom end of said autoradiograph to said top end of said autoradiograph;

means for generating a peak location data subset for each of said lanes based on said density profile along said lane, each said peak location data subset defining locations of density peaks along each of said lanes with reference to said bottom end of said autoradiograph;

means for merging together said peak location data subsets for each of said lanes so as to generate a combined set of peak location data;

means for generating, from said combined set of peak location data, a set of peak spacing data defining peak spacing along said autoradiograph with reference to said bottom end of said autoradiograph;

means for applying interpolative linear regression to said peak spacing data so as to generate a linearization formula for spacing of peaks along said autoradiograph;

means for applying said linearization formula to each of said lane data subsets so as to generate linearized lane data subsets corresponding to linearized peak spacing of density peaks in each of said lanes;

means for generating a refined peak location data subset for each of said lanes, comprising:

(i) means for removing noise from each of said linearized lane data subsets;

(ii) means for determining and subtracting a baseline from each of said linearized lane data subsets;

(iii) means for enhancing each of said linearized lane data subsets;

means for merging together said refined peak location data subsets for each of said lanes so as to generate a combined refined set of peak location data;

means for generating, from said combined refined set of peak location data, a refined set of peak spacing data defining peak spacing along said autoradiograph with reference to said bottom end of said autoradiograph;

means for applying said linearization formula to said refined set of peak spacing data so as to determine locations of misplaced and missing peaks along said autoradiograph and to enable appropriate insertion of said misplaced and missing peaks; and means for generating a set of output data corresponding to said plurality of lanes bearing said linearized spacing of peaks, said peaks corresponding to bases in said DNA sequence.

18. A system as claimed in claim 17 wherein said read length extending acrylamide comprise Genomyx HR 1000 brand high resolution gel.

19. A system for calling bases from an autoradiograph of a DNA nucleotide sequence, said autoradiograph being generated by gel electrophoresis and bearing an analog image comprising a plurality of adjacent lanes extending from a bottom end of said autoradiograph to a top end of said autoradiograph, said system comprising, in combination:

(a) means for scanning said autoradiograph to generate input data indicative of said analog image;

(b) means for segregating said input data into lane data subsets corresponding to each of said adjacent lanes;

(c) means for processing each of said lane data subsets to generate a density profile along each of said adjacent lanes from said bottom end of said autoradiograph to said top end of said autoradiograph;

(d) means for generating a peak location data subset for each of said lanes based on said density profile along said lane, each said peak location data subset defining locations of density peaks along each of said lanes with reference to said bottom end of said autoradiograph;

(e) means for merging together said peak location data subsets for each of said lanes so as to generate a combined set of peak location data;

(f) means for generating, from said combined set of peak location data, a set of peak spacing data defining peak spacing along said autoradiograph with reference to said bottom end of said autoradiograph;

(g) means for applying interpolative linear regression to said peak spacing data so as to generate a linearization formula for spacing of peaks along said autoradiograph;

(h) means for applying said linearization formula to each of said lane data subsets so as to generate linearized lane data subsets corresponding to linearized peak spacing of density peaks in each of said lanes;

(i) means for generating a refined peak location data subset for each of said lanes, comprising:
means for removing noise from each of said linearized lane data subsets, said means for removing noise comprising means for applying a low-bandpass filter to each of said linearized lane data subsets in a Fourier Transform domain;
means for determining and subtracting a baseline from each of said linearized lane data subsets; and
means for enhancing each of said linearized lane data subsets;

(i) means for merging together said refined peak location data subsets for each of said lanes so as to generate a combined refined set of peak location data;

(k) means for generating, from said combined refined set of peak location data, a refined set of peak spacing data defining peak spacing along said autoradiograph with reference to said bottom end of said autoradiograph;

(l) means for applying said linearization formula to said refined set of peak spacing data so as to determine locations of misplaced and missing peaks along said autoradiograph and to enable appropriate insertion of said misplaced and missing peaks; and (m) means for generating a set of output data corresponding to said plurality of lanes bearing said linearized spacing of peaks, said peaks corresponding to bases in said DNA sequence.

20. A system for calling bases from an autoradiograph of a DNA nucleotide sequence, said autoradiograph being generated by gel electrophoresis and bearing an analog image comprising a plurality of adjacent lanes extending from a bottom end of said autoradiograph to a top end of said autoradiograph, said system comprising, in combination:

(a) means for scanning said autoradiograph to generate input data indicative of said analog image;

(b) means for segregating said input data into lane data subsets corresponding to each of said adjacent lanes;

(c) means for processing each of said lane data subsets to generate a density profile along each of said adjacent lanes from said bottom end of said autoradiograph to said top end of said autoradiograph;

(d) means for generating a peak location data subset for each of said lanes based on said density profile along said lane, each said peak location data subset defining locations of density peaks along each of said lanes with reference to said bottom end of said autoradiograph;

(e) means for merging together said peak location data subsets for each of said lanes so as to generate a combined set of peak location data;

(f) means for generating, from said combined set of peak location data, a set of peak spacing data defining peak spacing along said autoradiograph with reference to said bottom end of said autoradiograph;

(g) means for applying interpolative linear regression to said peak spacing data so as to generate a linearization formula for spacing of peaks along said autoradiograph;

(h) means for applying said linearization formula to each of said lane data subsets so as to generate linearized lane data subsets corresponding to linearized peak spacing of density peaks in each of said lanes;

(i) means for generating a refined peak location data subset for each of said lanes, comprising:
means for removing noise from each of said linearized lane data subsets;
means for determining and subtracting a baseline from each of said linearized lane data subsets, said means for determining and subtracting a baseline comprising in combination (A) means for determining a local minimum across a density profile of said linearized lane data subset and (B) means for subtracting excess data fluctuations from said linearized lane data subset; and
means for enhancing each of said linearized lane data subsets;

(j) means for merging together said refined peak location data subsets for each of said lanes so as to generate a combined refined set of peak location data;

(k) means for generating from said combined refined set of peak location data, a refined set of peak spacing data defining peak spacing along said autoradiograph with reference to said bottom end of said autoradiograph;

(l) means for applying said linearization formula to said refined set of peak spacing data so as to determine locations of misplaced and missing peaks along said autoradiograph and to enable appropriate insertion of said misplaced and missing peaks; and (m) means for generating a set of output data corresponding to said plurality of lanes bearing said linearized spacing of peaks, said peaks corresponding to bases in said DNA sequence.

21. A system for calling bases from an autoradiograph of a DNA nucleotide sequence, said autoradiograph being generated by gel electrophoresis and bearing an analog image comprising a plurality of adjacent lanes extending from a bottom end of said autoradiograph to a top end of said autoradiograph, said system comprising, in combination:

(a) means for scanning said autoradiograph to generate input data indicative of said analog image;

(b) means for segregating said input data into lane data subsets corresponding to each of said adjacent lanes;

(c) means for processing each of said lane data subsets to generate a density profile along each of said adjacent lanes from said bottom end of said autoradiograph to said top end of said autoradiograph;

(d) means for generating a peak location data subset for each of said lanes based on said density profile along said lane, each said peak location data subset defining locations of density peaks along each of said lanes with reference to said bottom end of said autoradiograph;

(e) means for merging together said peak location data subsets for each of said lanes so is to generate a combined set of peak location data;

(f) means for generating, from said combined set of peak location data, a set of peak spacing data defining peak spacing along said autoradiograph with reference to said bottom end of said autoradiograph;

(g) means for applying interpolative linear regression to said peak spacing data so as to generate a linearization formula for spacing of peaks along said autoradiograph;

(h) means for applying said linearization formula to each of said lane data subsets so as to generate linearized lane data subsets corresponding to linearized peak spacing of density peaks in each of said lanes;

(i) means for generating a refined peak location data subset for each of said lanes, comprising:

means for removing noise from each of said linearized lane data subsets;

means for determining and subtracting a baseline from each of said linearized lane data subsets; and means for enhancing each of said linearized lane data subsets, said means for enhancing comprising means for emphasizing density peak shoulders throughout said linearized lane data subset;

(j) means for merging together said refined peak location data subsets for each of said lanes so as to generate a combined refined set of peak location data;

(k) means for generating, from said combined refined set of peak location data, a refined set of peak spacing data defining peak spacing along said autoradiograph with reference to said bottom end of said autoradiograph;

(l) means for applying said linearization formula to said refined set of peak spacing data so as to determine locations of misplaced and missing peaks along said autoradiograph and to enable appropriate insertion of said misplaced and missing peaks; and (m) means for generating a set of output data corresponding to said plurality of lanes bearing said linearized spacing of peaks, said peaks corresponding to bases in said DNA sequence.

* * * * *